United States Patent
Assman et al.

(10) Patent No.: US 8,923,953 B2
(45) Date of Patent: Dec. 30, 2014

(54) MEDICAL EXAMINATION APPARATUS HAVING AN ALARM SIGNAL EMITTER

(71) Applicants: Stefan Assman, Erlangen (DE); Björn Heismann, Erlangen (DE); Reto Merges, Erlangen (DE); Markus Schmidt, Nuremberg (DE); Sebastian Schmidt, Weisendorf (DE); Kera Westphal, Berlin (DE)

(72) Inventors: Stefan Assman, Erlangen (DE); Björn Heismann, Erlangen (DE); Reto Merges, Erlangen (DE); Markus Schmidt, Nuremberg (DE); Sebastian Schmidt, Weisendorf (DE); Kera Westphal, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/660,057

(22) Filed: Oct. 25, 2012

(65) Prior Publication Data

US 2013/0109965 A1    May 2, 2013

(30) Foreign Application Priority Data

Nov. 2, 2011    (DE) .......................... 10 2011 085 597

(51) Int. Cl.
*A61B 5/00* (2006.01)
*A61B 6/00* (2006.01)
*A61M 5/00* (2006.01)
*A61M 5/48* (2006.01)
*A61B 6/10* (2006.01)
*A61B 6/03* (2006.01)

(52) U.S. Cl.
CPC ................ *A61B 6/481* (2013.01); *A61M 5/007* (2013.01); *A61M 5/484* (2013.01); *A61B 6/10* (2013.01); *A61B 6/032* (2013.01); *A61B 6/541* (2013.01)
USPC ........... 600/431; 128/898; 600/420; 600/432; 600/433; 600/458

(58) Field of Classification Search
USPC ........... 600/420, 431–435, 458, 425; 424/9.1, 424/9.3–9.61
See application file for complete search history.

(56) References Cited

U.S. PATENT DOCUMENTS

| | | | |
|---|---|---|---|
| 4,006,736 A * | 2/1977 | Kranys et al. | 600/432 |
| 2003/0135116 A1* | 7/2003 | Ogasawara et al. | 600/437 |
| 2006/0178616 A1 | 8/2006 | Hartman et al. | |
| 2008/0021314 A1* | 1/2008 | Movahed | 600/431 |

FOREIGN PATENT DOCUMENTS

WO    WO 0064353 A2    11/2000

* cited by examiner

*Primary Examiner* — Parikha Mehta

(57) ABSTRACT

A medical examination apparatus including a control unit, an image-generating modality and a controllable injection apparatus for a contrast agent is provided. The control unit is connected to an alarm signal emitter and the control unit switches the modality and the injection apparatus to a safe mode as a function of an alarm signal.

4 Claims, 1 Drawing Sheet

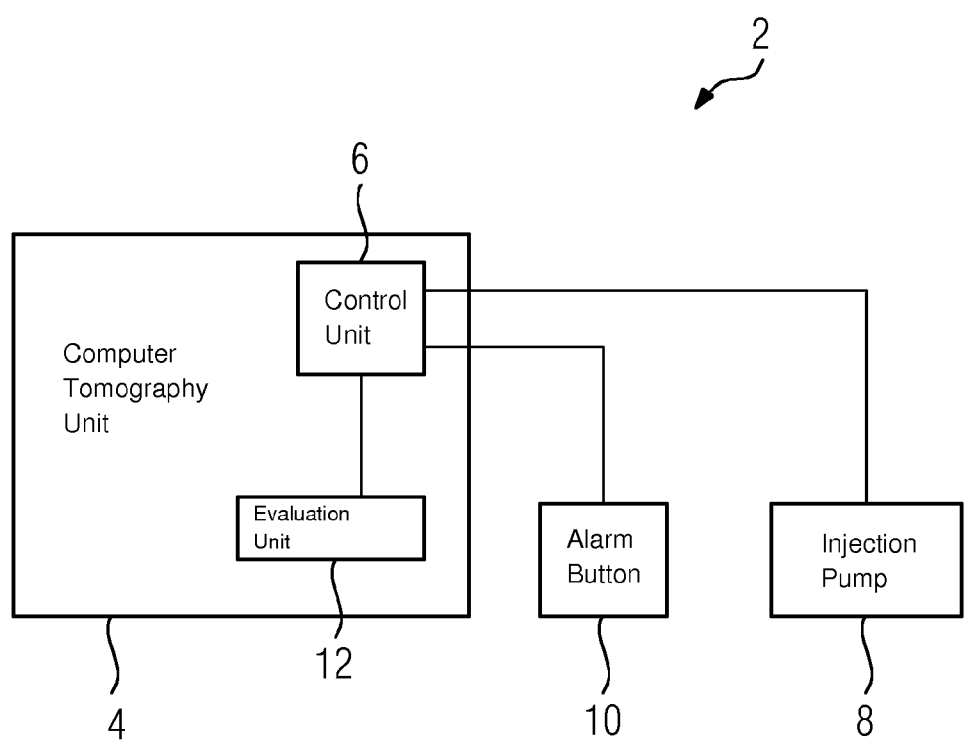

MEDICAL EXAMINATION APPARATUS HAVING AN ALARM SIGNAL EMITTER

CROSS REFERENCE TO RELATED APPLICATIONS

This application claims priority of European Patent Office application No. 10 2011 085 597.1 DE filed Nov. 2, 2011. All of the applications are incorporated by reference herein in their entirety.

FIELD OF INVENTION

The invention relates to a medical examination apparatus having a control unit, having an image-generating modality and having a controllable injection apparatus for a contrast agent.

BACKGROUND OF INVENTION

If a problem occurs when a patient is being examined using an imaging modality, it is generally desirable to terminate the ongoing examination. With the modalities currently used provision is generally made for such a termination of the ongoing examination to be performed by an operator, for example a medical technical assistant (MTA), as soon as he/she identifies a problem or judges a situation to be problematic.

A medical imaging apparatus having an image generation unit is also known from WO 00/64353, in which the information produced by means of the image generation unit can be used to terminate injection of a contrast agent in certain situations.

SUMMARY OF INVENTION

Against this background an object is to specify an improved medical examination apparatus.

This object is achieved by a medical examination apparatus having the features of the claims. The medical examination apparatus comprises a control unit, an image-generating modality and a controllable injection apparatus for a contrast agent, the control unit being connected to an alarm signal emitter, the alarm signal emitter having an alarm button for a patient and the control unit switching the image-generating modality and the controllable injection apparatus to a safe mode as a function of an alarm signal. Provision is preferably made here for the alarm signal emitter to generate different alarm signals as a function of the occurring problem. The control unit then switches the modality on the one hand and the injection apparatus on the other hand to a safe mode as a function of the alarm signal generated, with different safe modes preferably being provided for different alarm signals. This creates an automated safety system, which monitors every examination process and responds automatically according to defaults when a problem occurs, switching the medical examination apparatus to a safe mode, which results for example in the termination of the ongoing examination. If the image-generating modality is an x-ray device for example, the rapid termination of the ongoing examination and therefore of the irradiation of the patient keeps any non-beneficial, therefore undesirable, radiation exposure to a minimum. Manual termination of an ongoing examination in contrast generally takes place a longer period of time after the occurrence of the problem, so that greater radiation exposure for the patient can be assumed here.

The alarm signal emitter also has an alarm button for a patient, the actuation of which triggers the alarm, generating a corresponding alarm signal and routing it to the control unit. During an examination, for example using a computed tomography unit, it is at present normal for the patient to be given a device to hold, which can be used for an "emergency call". By actuating said device, also referred to as a "call ball", the operator of the computed tomography unit, who is typically in a different room during the examination, is alerted for example acoustically or visually to the emergency call, so that he/she can take appropriate measures, for example consulting the patient by way of a speaker device or terminating the ongoing examination. However termination then takes place with a time delay that is dependent on the operator, which is particularly undesirable when a contrast agent is used during the examination. Such contrast agents are generally injected into the body of the patient during the examination with the aid of the controllable injection apparatus, which is embodied for example as an injection pump or dosing pump. If the patient is unable to tolerate the contrast agent and side effects occur, the patient will trigger an emergency call. However until the operator terminates the examination and in particular deactivates the injection apparatus, the injection of the contrast agent continues. This undesirable delay can be avoided with the alarm button, which is positioned with the patient at least during the examination and is configured for example in the manner of a switch and in particular according to the principle of an "emergency off" switch. With an inventive automated response of the medical examination apparatus to the alarm triggered by actuation of the alarm button and therefore by the patient, the response is much more rapid and therefore the termination of the injection process is much more rapid, so the resulting dose of contrast agent is much smaller.

The alarm button and a system according to the principle of the "call ball" can also advantageously be combined, so that the patient can either contact the operator of the medical examination apparatus by "emergency call" or trigger the alarm directly, depending on the situation.

The alarm button is also integrated in a simple operating element with just a few functions or even just one "trigger alarm" function, which the patient can easily hold during an examination and which is therefore neither part of an operating console for the image-generating modality nor part of an operating console for the controllable injection apparatus nor part of an operating console for the medical examination apparatus. Alternatively such a simple operating element can be positioned in easy reach of the patient during an examination, in other words for example on or next to a patient couch.

A variant includes an evaluation unit for evaluating the image data generated by means of the image-generating modality is used as an additional alarm signal emitter. The image data is analyzed and compared with stored reference data, with a correspondence between image data and reference data triggering an alarm, whereupon the evaluation unit generates an alarm signal and routes it to the control unit. If the time pattern of an image signal is monitored for example in the region of the heart of the patient, while a contrast agent is injected into a vein at the same time, the contrast agent should reach the heart after a certain time and produce a change in the image signal there. If this change in the image signal does not occur, it is for example possible that the injection is not taking place into the vein as intended but into the surrounding tissue. Such an undesirable injection of the contrast agent into the tissue, referred to as paravasation, is potentially harmful for the patient and should therefore be effectively prevented. Therefore if no image signal change takes place after a predefined time interval in the monitored or examined region of the patient, the evaluation unit triggers the alarm and generates a corresponding alarm signal, which in turn prompts the control unit to deactivate the injection apparatus and thus prevent the further injection of contrast agent. Since the incorrect injection of contrast agent can generally only be perceived after a certain time by both operator and patient, additional automated monitoring by means of the image-generating modality and an evaluation unit, which is also preferably part of the image-generating modality, further improves patient safety.

In an embodiment, the evaluation unit triggers a corresponding alarm signal when a characteristic deviation of the generated image data from a target state is present. It should be noted here that every patient produces different image data and contrast agents produce different effects in every patient. For example the speed at which a contrast agent is disseminated in the body of a patient is a function of said patient's cardiovascular system. It is therefore not expedient here to terminate the examination after a fixed time interval of for example five seconds after the start of contrast agent injection. Instead a value of five seconds for example is predefined and termination takes place if there is a deviation of more than one second from this time interval.

In one embodiment of the examination apparatus a number of alarm signal emitters are provided, in other words for example both the alarm button and the evaluation unit for evaluating the image data, with each alarm signal emitter generating its own alarm signal that can be identified by the control unit in the event of an alarm and with the control unit responding according to defaults as a function of the respectively generated alarm signal, by switching for example the injection apparatus, the modality or both the injection apparatus and the modality to a safe mode.

Provision is further made for a further patient-specific differentiation, in which the state of the patient is also taken into account. It is usual for example, during examinations of the lung and heart using a computed tomography unit, to capture the heartbeat or pulse of the patient permanently by sensor for example by means of a so-called trigger EKG and to match the generation of individual images in time in such a manner that image generation takes place in each instance when the region to be examined is subject to relatively little movement. Such sensor data can advantageously also be used to estimate the dissemination speed of the contrast agent in the patient at the time of the examination, allowing a particularly suitable time deviation to be determined in this instance, after which the examination is automatically terminated, if a characteristic change in the image signal is not registered in the corresponding time period.

Also expedient is a variant of the examination apparatus, in which the injection pressure of the controllable injection apparatus is reduced in safe mode. If provision is made for example for automatic deactivation of the injection apparatus as a function of the injection pressure, in safe mode the injection apparatus is deactivated at a lower pressure, for example at 15 bar rather than at 30 bar. Since the dissemination speed of the contrast agent in the body of the patient is a function of the respective patient and said patient's state, it cannot be unambiguously concluded from the absence of any change in the image signal after a certain time interval whether or not the contrast agent is being injected correctly. In order to prevent unnecessary termination during examinations, provision is made according to one variant for the injection apparatus not to be deactivated after the corresponding time interval but simply for the injection pressure or rather the injection pressure limit to be lowered instead. When the contrast agent is injected in the required manner, injection of the contrast agent continues despite the lowering of the injection pressure, whereas when the contrast agent is injected incorrectly, for example into the surrounding tissue, a counterpressure very quickly builds up in the surrounding tissue which is above the injection pressure limit, so that the injection apparatus is then deactivated. This prevents unnecessary termination of an examination, without the risk of the contrast agent being injected incorrectly to any significant degree.

Alternatively provision is made for one variant of the examination apparatus, in which the controllable injection apparatus is deactivated in safe mode. The injection of contrast agent is therefore stopped as soon as an alarm signal is generated. This variant gives highest priority to preventing incorrect injection, whereby it is also accepted that some examinations will be terminated unnecessarily.

One embodiment of the examination apparatus is also advantageous, in which the image-generating modality or at least a radiation source used for image generation, as used for example with a computed tomography unit, is deactivated in safe mode. Since, when a problem occurs, it can generally be assumed that it will no longer be possible to generate image data that will be of use for a subsequent diagnosis during the ongoing examination, the deactivation of the modality and in particular its radiation source prevents any unusable, therefore undesirable, exposure of the patient to radiation.

According to one particularly expedient embodiment of the examination apparatus a central control unit of the image-generating modality is provided as the control unit. The central control unit of the image-generating modality then takes over the additional tasks which are otherwise performed by an independent control unit. Since an image-generating modality frequently comprises a central control unit anyway, this allows the safety concept presented here to be achieved virtually by retrofitting with relatively little outlay, even in the case of medical examination apparatuses that are already in use. In the most favorable instance changes then only have to be made in the area of the data exchange between the individual devices of the examination apparatus and in the control software of the individual components.

Provision is also made, for particularly good compatibility, in one variant of the examination apparatus for standard connections, such as for example CAN bus or Bluetooth, and standard protocols to be used for communication between the control unit, the image-generating modality and the controllable injection apparatus.

BRIEF DESCRIPTION OF THE DRAWINGS

More detail is described below based on a schematic drawing, in which:

FIG. 1 shows a block diagram of a medical apparatus.

DETAILED DESCRIPTION OF INVENTION

In the case of the medical examination apparatus 2 described below and illustrated in FIG. 1 a computed tomography unit 4 with a central control unit 6 is used to examine a patient using an imaging method. Depending on the examination method selected, provision is made for a contrast agent to be injected into the patient to assist the imaging method. For this purpose the medical examination apparatus 2 comprises an injection apparatus 8, which is preferably configured as an injection pump, also referred to as a dosing pump.

The injection apparatus 8 used in the exemplary embodiment is a controllable injection apparatus 8, which is connected for signaling purposes to the control unit 6 of the computed tomography unit 4 and which is activated by way of the control unit 6. This tailors the injection of the contrast agent to the respective selected image-generation method, in order thereby to influence the quality of the image data to be generated in a positive manner.

Before the start of an examination an operator, for example a medical technical assistant, uses a console (not shown in detail) to select a control program, which determines the order in which the computed tomography unit 4 on the one hand and the injection apparatus 8 on the other hand are activated during the examination.

Before the start of such an examination the patient is positioned on an examination table, which is part of the computed tomography unit 4. Also, if as here provision is made for an injection of contrast agent, an injection needle, which is part of the injection apparatus 8, is inserted into the body of the patient. Before the start of the examination the patient is also given an alarm button 10 to hold, which said patient is to actuate if necessary, for example if said patient notices a problem. The alarm button is connected for signaling purposes to the control unit 6 of the computed tomography unit 4 and, when actuated, generates an alarm signal, which is sent to the control unit 6.

The alarm button 10 therefore functions in the medical examination apparatus 2 as an alarm signal emitter, with the control unit 6 switching the injection apparatus 8 to a safe mode when the alarm button is actuated, in which safe mode the injection apparatus 8 interrupts the injection of the contrast agent. The operator of the medical apparatus 2 is also informed of this alarm, in that an acoustic or visual signal is output by way of the operating console.

In addition to the alarm button 10 in the exemplary embodiment a second alarm signal emitter is provided, in the form of an evaluation unit 12. The evaluation unit 12 is used to analyze the image data generated by means of the computed tomography unit 4, it being checked in particular whether the intended and anticipated influencing of the image information by the contrast agent is taking place to the expected degree and in the expected time interval. If not, the evaluation unit 12 triggers the alarm and generates an alarm signal, which is sent to the central control unit 6, as a function of the deviation of the actual state from the target state.

For example if the signal is not influenced after a period of five seconds after the start of contrast agent injection, it is assumed that the injection is not taking place correctly, in other words for example not into the vein in the arm but into the surrounding tissue, whereupon the central control unit 6 stops the injection of contrast agent by the injection apparatus 8. The operator is also informed of the triggered alarm and the stopped injection by means of an acoustic or visual warning message.

In the event of a suspected paravasation, in other words inadvertent injection into the surrounding tissue, it is necessary to prevent not only the further injection of contrast agent but also an injection of for example a common salt solution that usually follows. The further injection is therefore also stopped even if the injection of contrast agent has already been completed.

In the exemplary embodiment the control unit 6 of the computed tomography unit 4 itself finally functions as a third signal emitter. If an error message is output during the start phase of the examination or during an ongoing examination, for example due to a component failure, the control unit 6 itself triggers an alarm, whereupon either the scheduled examination is not started or the ongoing examination is stopped. When an ongoing examination is terminated, injection by means of the injection apparatus 8 is interrupted and the radiation source of the computed tomography unit 4, in other words the x-ray source, is deactivated or shielded.

An operating mode is also provided for the medical examination apparatus 2, in which dynamic adjustment of the injection parameters takes place. Provision is made for example for a pressure limit or a flow rate limit for the injection apparatus 8, to prevent harm to the patient, in particular due to paravasation. The evaluation unit 12 here monitors whether there is a flood of contrast agent in the blood, for example therefore in the right ventricle or the heart or the superior caval vein. If it can be assumed from the image data generated that the injection needle is positioned correctly and the contrast agent is being injected as intended, the pressure limit is raised, so that the contrast agent can then be injected at the flow rate specified for the actual examination.

The data exchange between the control unit 6 of the computed tomography unit 4 and the injection apparatus 8 here is preferably embodied as bidirectional, so that information can also be sent from the injection apparatus 8 to the control unit 6. If the contrast agent injection is terminated for example, before the specified dose has been injected, the data relating to the injected dose is transferred to the control unit 6. Even if image generation by means of the computed tomography unit 4 has also been terminated prematurely, it is still possible for the image data generated up to that point to be used in the later evaluation. The information relating to the injected dose can then be taken into account during image reconstruction or image processing.

We claim:

1. A method for examining a patient, comprising:
    generating image data of the patient by an image generation device, wherein the image generation device comprises a control unit;
    sending out a first alarm signal to the control unit by an alarm button when the alarm button is activated by the patient;
    triggering a second alarm signal to the control unit by an alarm signal emitter when there is a deviation of the image data from a target state; and
    injecting a contrast agent by a controllable injection pump, wherein the control unit switches the image generation device and the controllable injection pump to a safe mode as a function of the first alarm signal and the second alarm signal respectively, and
    wherein the control unit switches the image generation device and the controllable injection pump to the safe mode if an error occurs during an examination.

2. The method as claimed in claim 1, wherein an injection pressure of the controllable injection pump is lowered in the safe mode.

3. The method as claimed in claim 1, wherein the controllable injection pump is deactivated in the safe mode.

4. The method as claimed in claim 1, wherein the image generation device is deactivated in the safe mode.

* * * * *